(12) United States Patent
Tonge et al.

(10) Patent No.: US 6,436,905 B1
(45) Date of Patent: Aug. 20, 2002

(54) LIPID-CONTAINING COMPOSITIONS AND USES THEREOF

(75) Inventors: Stephen R Tonge, Birmingham; Brian J Tighe, West Midlands, both of (GB)

(73) Assignee: Aston University, Birmingham (GB)

( * ) Notice: Subject to any disclaimer, the term of this patent is extended or adjusted under 35 U.S.C. 154(b) by 0 days.

(21) Appl. No.: 09/510,223

(22) Filed: Feb. 22, 2000

Related U.S. Application Data (63) Continuation of application No. PCT/GB98/02546, filed on Aug. 24, 1998.

(30) Foreign Application Priority Data

Aug. 22, 1997 (GB) .............................................. 9717905

(51) Int. Cl.⁷ .......................... A61K 31/70; A61K 31/20
(52) U.S. Cl. .......................... 514/23; 514/558; 514/560
(58) Field of Search .......................... 514/772, 23, 558, 514/560

(56) References Cited

U.S. PATENT DOCUMENTS 5,374,420 A * 12/1994 Gerstein ................... 424/70.11
5,436,010 A * 7/1995 Lau et al. ................... 424/450

FOREIGN PATENT DOCUMENTS

WO WO 95/11700 5/1995

OTHER PUBLICATIONS

Derwent Publications Ltd., AN 89–117244 (XP002099889) (JP 01 061424).
Derwent Publications Ltd., AN 93–316735 (XP0020999890) (JP 05 228358).
Seki et al, Macromolecules, 17:1692–1698 (1984).

* cited by examiner

Primary Examiner—Alton Pryor
(74) Attorney, Agent, or Firm—Pillsbury Winthrop LLP (57) ABSTRACT

Lipid-containing compositions are disclosed which provide surfactants and solubilizing agents useful in medicine, biochemistry and other industries.

32 Claims, 1 Drawing Sheet

Figure 1

LIPID-CONTAINING COMPOSITIONS AND USES THEREOF

This is a Continuation of: International Appln. No. PCT/GB98/02546 filed Aug. 24, 1998 which designated the U.S.

FIELD OF THE INVENTION

The present invention relates primarily to the field of biochemistry and medicine. More particularly, it is concerned with lipid-containing compositions which, in one main aspect of the invention, provide useful surfactants or solubilizing agents for certain substances, particularly drugs or other bioactive materials, and can be especially useful for producing aqueous solutions of substances that are lipid soluble but have poor aqueous solubility. Thus, they can be used as formulating and delivery agents for the formulation and/or delivery, possibly site-specific delivery, of drugs or other bioactive materials in connection with therapeutic (or cosmetic) treatment of mammals. These lipid-containing compositions also provide artificial surfactants having useful therapeutic applications in medicine, e.g. as lung surfactants or as lubricating surfactant materials for inclusion in ocular formulations or other lubricating formulations for medical use. The compositions can, however, have other uses and applications, particularly as solubilizing agents, in different areas of biochemistry or biotechnology and in the food industry for example.

BACKGROUND

There is a continual need for new or improved drug formulation and/or delivery agents, particularly for example in connection with administration of active drugs that have poor aqueous solubility. Improved drug delivery methods are also important in connection with the development of gene therapy where the drug to be administered or delivered is therapeutic genetic DNA or RNA or DNA/RNA fragments which need a carrier vehicle for protection and for facilitating take-up by target cells. Also, there is a need for improved delivery agents for achieving efficient delivery of other sensitive or unstable drugs as well as for achieving efficient delivery of drugs of poor aqueous solubility. There is moreover often a need for efficient and non-toxic solubilizing agents in other fields, for example in the food and cosmetic industries.

Also, a need has been identified for solubilising agents that can be used for solubilising proteins, especially drug receptor proteins for example within phospholipid membranes in such a way as to retain their native conformation and thereby to enable their structure to be determined e.g. by NMR spectroscopy. Elucidation of their structures in this manner may enable more efficient agents to be designed to interact with such receptors and act as potential drugs. Some embodiments of this invention may help to meet these various needs.

With regard to lung surfactants, as is well known, to achieve a proper respiratory function and gaseous exchange, all mammals secrete in their lungs a surfactant for controlling during exhalation and inhalation the surface tension of the fluid film that covers the epithelial respiratory surface lining the alveoli. The alveoli form in effect a series of minute interconnecting fluid-lined sacks, arranged so as to maximize the surface area for gaseous exchange across a fluid/air interface. However, this arrangement presents a potential physico-chemical problem for the body in that the alveoli sacks approximate in form to small bubbles subject to Laplace's law whereby the gaseous pressure within the bubble is inversely proportional to the radius or diameter and is directly proportional to the surface tension of the fluid in the boundary film. Thus, as the diameter of an alveolar sack decreases during exhalation, the pressure therein will tend to increase and this could lead to pressure disparities. Pressure disparities between the alveoli, however, would tend to force air from the smaller alveolar sacks into the larger ones, resulting in a collapse of the former. If this situation occurred in vivo subsequent expansion of the lungs would be far more difficult and the entire lungs may even collapse.

To avoid these problems mammals produce a natural surfactant to lower the surface tension of the fluid film of the alveolar surfaces when the surface area is constricted during exhalation. Conversely, the force needed to inflate the lungs is also equalised. In both cases the lungs are able to deflate and inflate uniformly with a variation in terminal size of different alveoli. Such a degree of functional control is achieved by reducing surface tension in direct proportion to the reduction in surface area and this, in turn, is achieved by an increase in the concentration of surfactant per unit area at the surface. The mechanism is similar to that employed in a Langmuir trough, whereby constriction of an insoluble monolayer squeezes water out of the interface so minimizing the cohesive forces between water molecules acting to 'pull' the surface together.

In human neonates, lung surfactant is synthesized around two months prior to term, enabling the lungs to inflate and normal breathing to commence at birth. However, in infants born more than two months premature the quantities of lung surfactant may be greatly reduced or completely absent and this situation prevents the lungs from inflating, resulting in the development of neonatal respiratory distress syndrome (RDS) which remains the most common cause of neonatal mortality.

Endogenous lung surfactant generally consists of 90% (wt./vol.) lipid in combination with 10% protein. The lipoidal fraction is made up of 90% phospholipid of which 80% is phosphatidylcholine (PC), with some 40–45% in the form of the dipalmitoyl ester (DPPC) and the remainder as monoenoic PC. The lipid usually also contains 10–15% phosphatidylglycerol (PG) and 7–8% cholesterol.

In early attempts to develop artificial phospholipid-based surfactants using only phospholipids, or lipoidal mixtures simulating the lipid composition of native lung surfactant, it was found that such artificial surfactants were significantly less effective than the natural product in treating RDS. In particular, it was found that the phospholipids used often failed to completely adsorb and spread at the alveolar air/fluid interface in the absence of certain apoproteins, termed surfactant proteins, which occur in endogeneous surfactant. It is believed that these surfactant proteins act to modify the assembly of phospholipids and transport the latter from T cells lining each alveolus across the aqueous subphase to form a lipid monolayer at the air interface.

This difficulty has been partly overcome by the recent introduction into clinical practice of artificial lung surfactants for treatment of RDS based upon animal derived apoprotein extracts (see Table of Commercial Surfactants below and also Table I at the end of the present description). However, although this development has revolutionized treatment of this disorder, it can result in dramatic cost increases being imposed on health care providers as these known artificial lung surfactants are generally very costly, and also they pose serious questions as to the suitability of using animal proteins in treatment of human neonates.

Table of Existing Commercially Available Artificial Lung Surfactants

| Name | Dose/12 Hrs/Kg | Concentration Surfactant | [%] | Conc. Ratio |
|---|---|---|---|---|
| Exosurf* | 67.5 mg/5 mls | 13.5 mg/ml | 1.35 | 1 |
| Curosurf | 120 mg/1.5 mls | 80 mg/ml | 8.0 | 5.9 |
| ALEC* | 100 mg/1.2 mls | 83.3 mg/ml | 8.33 | 6.2 |
| Survanta | 200 mg/8 mls | 25.0 mg/ml | 2.5 | 1.85 |

*these specific artificial lung surfactants are not particularly efficient and do not contain proteins.

There is accordingly a need for an effective artificial lung surfactant that can be manufactured cheaply from synthetic materials, and the provision of such an artificial surfactant represents one object of the present invention. It will be appreciated that the implications of this work in developing an effective and cheap artificial lung surfactant may have far reaching consequences in terms of the numbers of individuals that could benefit. A conservative estimate of the mortality rate arising from respiratory distress syndrome (RDS) would suggest, based upon published statistics ("Infant mortality rates" from US Dept. Health and Human Services, 1992), that globally there are some 100,000 cases per annum, mainly in developing countries. Hence, a cheaply available lung surfactant may significantly influence both the survival rate and subsequent health of a considerable number of children world-wide.

Apart from a need for artificial lung surfactants, pharmaceutically acceptable surfactants are also needed for treatment of other medical conditions affecting membraneous or mucosal surfaces, e.g. tear film surfactants for ocular use in treatment of the condition known as "dry eye" syndrome, and surfactants for lubricating or treating the surfaces of articulated joints in connection with arthritic conditions. There is also a need for lubricating surfactants to lubricate surfaces of medical devices and prostheses, e.g. artificial joints and contact lenses, that are fitted in the human or animal body.

SUMMARY OF THE INVENTION

From one aspect the present invention provides a lipid-containing composition which consists of a substantially clear aqueous solution containing a membrane-forming polar lipid and a synthetic amphipathic polymer, said polymer including both hydrophobic groups and anionic hydrophilic groups and acting as a lipid-solubilizing agent which interacts with and solubilizes the lipid in the aqueous medium. In many embodiments the lipid-containing compositions of this invention will be used or formulated for use in therapy. Thus, from another aspect the invention also resides in the use of a lipid-containing composition for the manufacture of a medical preparation, said composition consisting of a substantially clear aqueous solution containing a membrane-forming polar lipid and a synthetic amphipathic polymer, said polymer including both hydrophobic groups and anionic hydrophilic groups and acting as a lipid-solubilizing agent which interacts with and solubilizes the lipid in the aqueous medium.

From another aspect the invention also provides a lipid-containing composition consisting of a substantially clear aqueous solution containing a membrane-forming polar lipid together with a synthetic amphipathic polymer and a lipid-soluble target substance of poor aqueous solubility, said polymer including both anionic hydrophilic groups and hydrophobic groups and acting as a lipid solubilizing agent which interacts with and solubilizes the lipid together with said target substance in said aqueous medium. In this case the additional lipid-soluble target substance may be present either to be delivered, (e.g. drug delivery) or, in the case of a lipid-soluble protein, to assist in the targeting of the lipid/polymer combination to particular tissues within the body, or in some cases to hold the protein in a correct confirmation for analysis.

In preferred embodiments the lipid will usually comprise a phospholipid and the synthetic amphipathic polymer with which it is combined will have a balance of hydrophobic and anionic hydrophilic groups evenly arranged along a linear backbone.

An example of one lipid-solubilizing synthetic amphipathic polymer including both hydrophobic groups and anionic hydrophilic groups which can be used in carrying out the invention is the homopolymer poly(2-ethyl acrylic acid) (PEAA) that has previously been reported as interacting in aqueous solutions at pH >7 with phosphatidylcholines such as dilauroylphosphatidyicholine (DLPC) and dipalmitoylphosphatidylcholine (DPPC) to yield suspensions of multilamellar vesicles which clear when the pH is lowered below a critical value of approximately 6.5. See for example K. Seki et al. (1984) "pH-Dependent Complexation of Poly(acrylic acid) Derivatives with Phospholipid Vesicle Membranes", *Macromolecules*, 17, 1692–1698, D. A. Tirrell et al. (1985) "pH Sensitisation of Phospholipid Vesicles via Complexation with Synthetic Poly(carboxylic acid)s", *Ann. N.Y. Acad. Sci* 446, 237–248, and K. A. Borden et al. (1987) "Polyelectrolyte adsorption induces a vesicle-to-micelle transition in aqueous dispersions of dipalmitoylphosphatidylcholine", *Polymer Preprinits*, 28, 284–285).

The solubilization effect described in the literature referred to was attributed to a break-up and reorganisation of the vesicle structures accompanying conformational changes occurring in the polymer upon lowering of the pH, leading to the formation of lipid/polymer complexes producing small micellar discoidal particles or assemblies. Suggestions were also made in the above-mentioned papers that the materials described could have useful medical applications if they are prepared so that therapeutic substances are entrapped within the vesicles because upon administering such preparations in the course of medical treatment these vesicles, known as liposomes, would break up and quickly release their contents upon entering a target region of low pH. It should be noted, however, that these proposals related only to the use of compositions comprising intact vesicles or liposomes within the interior of which an aqueous soluble drug or other therapeutic agent is entrapped, the vesicles or liposomes themselves being used merely as mechanical containers. No recognition was expressed of any value, for therapeutic purposes or otherwise, of the lipid/polymer complexes of the micellar particles or assemblies produced after the break-up of the liposomes. It has now been appreciated, however, that such lipid/polymer complexes can in themselves provide useful compositions having regard to advantageous surface activity and/or solubilizing characteristics, combined with favourable small dimensional characteristics. It is these hitherto unrecognised properties and practical applications thereof which are exploited in the present invention.

The term "membrane-forming polar lipid" is used herein to denote lipids having a highly polar head portion attached to a nonpolar hydrophobic tail, generally composed of a pair of relatively long hydrocarbon chains, such that in aqueous media the lipid molecules tend to associate and form membrane structures at interfaces, possibly as lipid monolayers or bilayers.

In preferred embodiments these polar lipids used in connection with the invention will usually be phospholipids based on glycerol in the form of phosphatidic acid derivatives in which the non-polar acyl ester groups contain between 8 and 25 carbon atoms. These acyl ester groups, however, are preferably selected from lauryl, palmitoyl and myristoyl, and the polar head of the molecule will be provided by the phosphate group with a choline substituent, i.e. the lipid will be a phosphatidylcholine. Nevertheless, it is also possible in some embodiments to use other polar lipids, especially phospholipids, based on different structures, for example sphingosine or a ceramide from which may be derived the phospholipid sphingomyelin.

It should be pointed out that many of these polar lipids, especially phospholipids such as phosphatidylcholines, undergo phase transitional changes in aqueous media at predetermined temperatures at which they may change from a relatively ordered to a relatively disordered state. Dipalmitoylphosphatidylcholine (DPPC), for example, has a main thermal phase transition temperature ($T_m$) of around 42° C., although for dilauroylphosphatidylcholine (DLPC) the main thermal phase transition temperature is about −2° C. so that it is in a disordered bilayer or liquid crystalline phase at room temperature.

In carrying out the invention, instead of PEAA other similar vinyl homopolymers of an acrylic acid derivative having a hydrophobic side chain, e.g. 2-propyl acrylic acid, or other poly(carboxylic acid) polymers having pendant hydrophobic side groups in addition to anionic hydrophilic groups, may be used. In preferred embodiments, however, the selected synthetic lipid-solubilizing amphipathic polymer will be a linear alternating vinyl copolymer formed by free radical addition polymerisation of an unsaturated dicarboxylic acid, or an anhydride or monoester of said dicarboxylic acid, with a monoenoic vinyl monomer or monomers in alternating relationship.

Thus, from another aspect the invention provides a lipid-containing composition consisting of a substantially clear aqueous solution containing a membrane-forming polar lipid and a synthetic amphipathic polymer, said polymer including both anionic hydrophilic groups and hydrophobic groups and acting as a lipid-solubilizing agent which interacts with and solubilizes the lipid in the aqueous medium, characterised in that the synthetic amphipathic polymer is a copolymer of a first monomer which is an unsaturated dicarboxylic acid, or an anhydride or monoester thereof, and a second monomer which is a monoenoic compound such as a vinyl compound or a compound such as indene or napthalene, said first and second monomers being arranged in alternating relationship to form a linear backbone.

The monoenoic monomer or monomers will generally be selected from indene or napthalene and compounds of formula R—CH=CH$_2$ where R is hydrogen, $C_1$–$C_8$ alkyl or alkoxy, or is phenyl or benzyl which may be optionally substituted with an alkyl or other hydrophobic group, with the proviso that if R is alkoxy, i.e. if the compound is an alkyl vinyl ether, $C_3$–$C_6$ alkoxy is preferred. With regard to the dicarboxylic acid, that provides said first monomer, this will generally be a compound of formula:

where $R^1$ and $R^2$ are each independently hydrogen or $C_1$–$C_9$ alkyl, at least one of $R^3$ and $R^4$ is hydrogen and the other is hydrogen or $C_2$–$C_9$ alkyl, and the copolymer structure is such that the second monomer units alternate with the dicarboxylic acid or ester units providing a regular arrangement of alternate pendant anionic hydrophilic side groups and hydrophobic side groups along a linear backbone, subject to the proviso that if, in the above-defined monoenoic vinyl monomer, R is hydrogen or is methoxy or ethoxy ($C_1$ or $C_2$ alkoxy), $R^3$ and $R^4$ should not then both be hydrogen. Usually, in preferred embodiments, $R^1$ and $R^2$ are both hydrogen, and also alkyl vinyl ether monomer-containing copolymers with alkyl groups longer than seven carbon atoms will not be suitable because of low aqueous solubility. As indicated, the dicarboxylic acid may be presented in the form of its anhydride.

Also, at least in preferred embodiments, the number of carbon atoms in the hydrophobic side groups of the polymer or copolymer should usually be equal to or greater than the number of carbon atoms in the backbone of the polymer, and when ionized the average charge ratio per backbone carbon is less than or equal to unity.

Especially suitable polymers may be formed as alternating copolymers of maleic acid (or the anhydride thereof) with styrene, indene or a $C_{1-4}$ alkyl, e.g. methyl, substituted styrene or indene, or with propyl (or isopropyl) or butyl vinyl ether. It is also possible to use a mixture of the styrene, or indene, or alkylated styrene or indene, and alkyl vinyl ether components. A number of suitable copolymers that may be used are commercially available from Aldrich Chemical Co., e.g. those marketed under the Aldrich Chemical Co. catalogue number 43,529-5 (CAS Registry No. 25736-61-2). Pharmaceutical grade polymers or copolymers that can be used are available from Kuraray Co. Ltd. of Japan.

In preferred embodiments, the polymer will have physiologically or pharmaceutically acceptable non-toxic properties, and the molecular weight (number average) or relative mass of the polymer will generally be within the range of 2,000 to 20,000 daltons. In some cases, however, unless the composition is to be formulated for parenteral injection the molecular weight may be higher, e.g. up is 500,000 daltons, although usually the molecular weight will not be greater than 100,000 daltons, and will preferably be no greater than 50,000 daltons as for example with poly (maleic anhydride-butyl vinyl ether) that has a number average molecular weight equal to 43 kDa approximately. The polymer must not, however, be in the form of a "block copolymer".

Examples of typical number average molecular weights of the polymers used in carrying out this invention, especially for solubilizing drugs, are as follows:

| | |
|---|---:|
| Poly(maleic anhydride-styrene) | 7,000 |
| Poly(maleic anhydride-propyl vinyl ether) | 5,500 |
| Poly(maleic anhydride-butyl vinyl ether) | 43,300 |

The particular synthetic method used in synthesising the maleic anhydride styrene copolymers described herein involves a step of quenching the reaction mixture after a certain interval and favours the formation of alternating copolymers which is an essential feature in the formation of a coil with an amphipathic character such that one facet is hydrophobic and one is hydrophilic. This cannot generally be achieved in copolymers which are 'blocky' or produced by other means, e.g. in the poly(maleic anhydride-styrene) copolymers supplied by Sigma Chemical Co. St. Louis, Mo. and sold as 50% styrene (number average molecular weight 350,000), or those sold by Scientific Polymer Products Inc. Ontario, N.Y. as 50/50 maleic anhydride-styrene copolymers with a molecular weight of 50,000.

In many cases, especially for pharmaceutical applications, poly(maleic anhydride-styrene) (PMAS) will be a preferred polymer. This polymer, of molecular weight 14,000 daltons, is disclosed in U.S. Pat. No. 4,732,933 (Yamanouchi) and is already used in an approved pharmaceutical preparation conjugated to the proteinaceous antitumor agent neocarzinostatin, the polymer there acting to raise both the molecular weight and lipophilicity so leading to accumulation of the drug in certain target tissues. This polymer drug conjugate is known as SMANCS. For drug delivery, non-degradable vinyl-based polymers such as PMAS offer a potential advantage over synthetic polypeptides of analogous or identical structure to apoproteins in that they will not be rapidly hydrolysed in the blood plasma, and hence will be more likely to deliver any drug to the target site before degradation of the micelle and loss of its contents. In addition, they lack the allergic or pharmacological potential of non-native peptides or proteins.

It is believed that in aqueous media, at least over a particular pH range, the solubilizing synthetic amphipathic polymers specified will generally adopt a helical coil configuration with the hydrophobic side groups presented along one facet and the anionic hydrophilic groups presented along the opposite facet, and that they interact with the lipid in the aqueous medium to form discoidal micellar particles or assemblies of sub-liposomal dimensions in which the lipid forms a bilayer core. In any event. it has been found that these micellar particles or assemblies in the compositions of the present invention, at least when freshly prepared, have a maximum diameter or cross-sectional dimension of less than 50 nm under physiological conditions of temperature and pH. Sizes of the discoidal micellar assemblies usually appear to be in the range of 10–40 nm in diameter, typically 20 nm, and 5–7 nm thick. This compares favourably with the dimensions of lipoprotein micellar assemblies found in nature, such as the well characterized system between apolipophorin III and dimyristoylphosphatidylcholine (DMPC) that has been identified in insects, where the micelles are reported to have a diameter of 18.5+/−2.0 nm and a thickness of 4.8+/−0.8 nm (see Wientzek, M., Kay, C. M., Oikawa, K. and Ryan, R. O (1994), "Binding of Insect Apolipophorin III to Dimyristoylphosphatidylcholine Vesicles." *J. Biological Chem.* 269 (6). 4605–4612). In comparison, typical phospholipid-containing liposomes currently used in drug delivery systems have a diameter of 50–100 nm for unilamellar vesicles and 400–3500 nm for multilamellar vesicles.

The compositions in accordance with the invention will generally be prepared by mixing the polymer and the polar lipid in the aqueous medium and adjusting the pH to effect solubilization. Then, particularly if required for administration to a mammal and for medical use, the pH will usually be further adjusted to a physiologically acceptable value.

Accordingly, from yet a further aspect the invention provides a method of preparing a lipid-containing composition as hereinbefore specified which comprises the steps of mixing the constituents together in an aqueous medium at a pH above a critical solubilizing value thereby to form a cloudy or turbid aqueous dispersion, and then treating the mixture with an acidifying agent to lower the pH below said critical solubilizing value whilst the temperature is above a predetermined phase transition temperature characteristic of the lipid, thereby enabling the synthetic amphipathic polymer to carry out its function as a solubilizing agent and causing the dispersion to clarify.

The invention also provides a method of solubilizing in an aqueous medium a lipid-soluble target substance that has poor aqueous solubility, said method comprising the steps of mixing together in said aqueous medium the said target substance, a membrane-forming polar lipid, and a synthetic amphipathic polymer, at a pH above a critical solubilizing value thereby to form a cloudy or turbid aqueous dispersion, and then treating the mixture with an acidifying agent to lower the pH below said critical solubilizine value whilst the temperature is above a predetermined phase transition temperature characteristic of the lipid, whereby said synthetic amphipathic polymer, which includes both anionic hydrophilic groups and hydrophobic groups, interacts with and solubilizies said lipid together with said target substance in the aqueous medium.

Also, according to the invention, a method of preparing a lipid-containing composition comprises the steps of mixing together in an aqueous medium a membrane-forming polar lipid and a synthetic amphipathic polymer at a pH above a critical lipid-solubilizing value thereby to form a cloudy or turbid aqueous dispersion, and then treating the mixture with an acidifying agent to lower the pH below said critical lipid-solubilizing value whilst the temperature is above a predetermined phase transition temperature, e.g. greater than 25° C., which is characteristic of the lipid, whereby said synthetic amphipathic polymer interacts with and solubilizies said lipid so as to clarify the dispersion, characterised in that after the dispersion clears the temperature is reduced below said phase transition temperature to stabilise the solution, followed by the step of treating the solution with an alkaline reagent to raise the pH and adjust it to a final value above said critical lipid-solubilizing value.

In general, before use the lipid-containing compositions of the present invention will be incorporated in formulations made up to suit the particular purpose and manner of use, or mode of administration in the case of pharmaceutical applications. For making up formulations for pharmaceutical use, the lipid-containing compositions may be mixed with one or more pharmaceutically acceptable carriers, additives, diluents or excipients, and optionally with any other therapeutic ingredients desired. Such formulations may be prepared by any of the methods well known in the art of pharmacy, and may be designed for inhalation, topical or parenteral (including intravenous, intra-articular, intramuscular and subcutaneous) administration for example. Formulations suitable for parenteral administration conveniently comprise sterile aqueous preparations that, for intravenous injection, are preferably isotonic with the blood of the recipient. Thus, the invention also includes pharmaceutical formulations comprising compositions of lipid/polymer complexes as herein disclosed.

It will also be understood that the lipid-containing compositions of the present invention may be converted into alternative forms, e.g. for storage and transport, and in particular the compositions may be converted into a freeze-dried state, either before or after being incorporated into a pharmaceutical or other formulation, from which they can be reconstituted, if necessary, when required for use. All such alternative forms are to be regarded as falling within the scope of the invention.

As already indicated, particularly important applications of the invention related to advantageous surface active characteristics of the lipid-containing compositions described lie in the provision of lung surfactant formulations for use in treatment of respiratory distress syndrome (RDS), and in the provision of ocular formulations e.g. for treatment of dry eye syndrome.

Other important applications of the invention related to the advantageous solubilizing properties of the lipid/polymer complexes include the use of the compositions for drug delivery purposes. In this case the polar lipid component is preferably a phospholipid and contains a lipid soluble drug, e.g. a steroid, or other bioactive therapeutic agent, e.g. a DNA-containing vector or plasmid for gene therapy, whereby the polymer/phospholipid complex is adapted for use as a drug delivery vehicle;

In relation to the proposed use of the compositions as lung surfactants, it may be, noted that for some time synthetic polymers have been sought having secondary structures analogous to those of the native lung surfactant apoproteins in order to mimic the lipid/protein interactions found with the latter. It is surprising, however, that although a number of polymers with similar structural elements have been synthesised, these have failed to show functional behaviour analogous to those of the native target apoproteins, but on the other hand some relatively simple copolymers such as are described in connection with the present invention and which have no apparent structural similarity have been found to perform functionally in a manner that closely resembles that of the native apoproteins.

Recently a fairly clear view has emerged regarding the macromolecular structure of native lung surfactant, and the active components thereof have been identified as a bilayer structure consisting mainly of the phospholipid, dipalmitoylphosphatidylcholine (DPPC), in association with two principal apoproteins termed SP-B and SP-C which appear to be involved in spreading of the lipid at the air/fluid interface.

Figure 1:
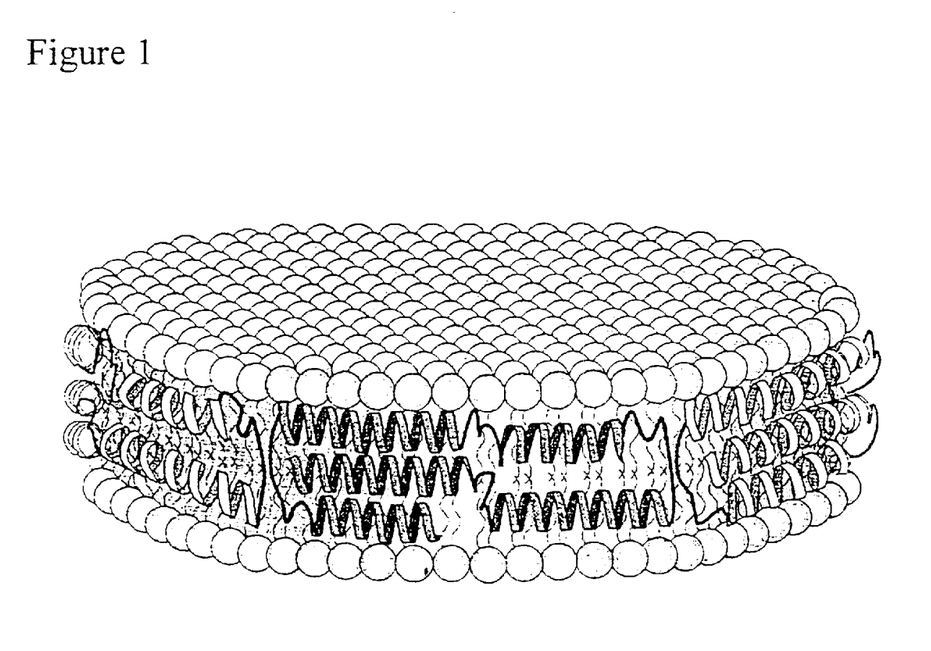
FIG. 1 depicts the lipid-polymer complex.

Of these two apoproteins, multi-dimensional NMR analysis has revealed SP-C as having a secondary structure in the form of a transmembrane coil which is dipalmitoylated at one end and spans the phospholipid bilayer with the dipalmitoyl chains projecting outwards such as to render the surface hydrophobic. On the other hand, it is believed that apoprotein SP-B forms an amphipathic coil analogous to the coiled structures found in serum lipoproteins and surrounds discoidal segments or micelles of the phospholipid bilayer in the form of a hydrophilic annulus. The arrangement envisaged is similar to the now well established arrangement described by Ryan, R. O. "Structural studies of lipoproteins and their apolipoprotein components", *Biochem. Cell Biol.* 74, 155–164 (1996) in connection with certain plasma lipoproteins, illustrated in FIG. 1 of the accompanying drawing.

In developing the compositions of the present invention for use as a lung surfactant the polar lipid, generally a phospholipid, may be advantageously associated also with an additional synthetic polymer, a synthetic amphipathic polyamide polymer, that is adapted to simulate the transmembrane apoprotein known as SP-C of natural endogenous lung surfactant. Such additional polyamide polymer may be poly(lysine ethyl ester adipamide) (PLETESA) which has a coiled configuration that changes according to whether it is in a polar or non-polar medium.

When the compositions are intended for use as lung surfactants, the inclusion of additional hydrophobic esters designed to span or extend through the lipid bilayer in a manner somewhat analogous to the SP-C apoprotein of natural lung surfactant may be advantageous for assisting orientation at air/fluid interfaces of the lipid/polymer complexes of these compositions. A fatty acid ester, e.g. lauric acid lauryl ester, can be used for this purpose.

DESCRIPTION OF ILLUSTRATIVE EXAMPLES

The following examples and description of stages in the preparation and use of various exemplary compositions containing polymer/phospholipid complexes serve further to illustrate the present invention and will enable the skilled person in the art more readily to appreciate the nature of the invention and to put it into practical effect. They should not, however, be construed in any way as a limitation thereof.

EXAMPLE 1

Polymer Synthesis
1 Preparation of Vinyl Copolymers of Maleic Anhydride and Either Styrene or Alkyl Vinyl Ethers In a typical procedure, vinyl copolymers of maleic anhydride and either styrene or alkyl vinyl ethers are synthesised in a resin flask under a nitrogen atmosphere by refluxing at 80° C. 0.125 moles of each monomer is dissolved in 225 mls of an equimolar mixture of reagent grade toluene and ethyl acetate, and into this mixture (450 mls) is added approximately 1% or less by weight of an initiator such as di-(4-tert-butyl cyclohexyl)peroxydicarbonate (0.25 g) or benzoyl peroxide (0.4 g). The reacting solution becomes cloudy upon formation of the polymer in the case of poly(maleic anhydride styrene) since this polymer is insoluble in the solvent system used. The reaction is allowed to proceed for ten minutes after the first appearance of precipitated polymer and is stopped by quenching in an ice bath. The resultant polymer is then removed by filtration, refluxed with excess solvent to remove any unreacted monomer, and finally refiltered, washed in methanol and dried in vacuo.

Where the polymer is soluble in the solvent mixture, as is the case in copolymers containing alkyl vinyl ethers, the reaction is allowed to proceed for thirty minutes to two hours. The polymer is then recovered by precipitation into supercooled diethyl ether and collected by filtration and dried in vacuo.

In carrying out the invention, alternating copolymers of maleic anhydride and methyl styrene, or other alkyl styrene compounds or indene, may be used in place of maleic anhydride/styrene.

EXAMPLE 2

Formation of Micellar Polymer/Lipid Complex

The micellar polymer/lipid complex compositions are formed by hydrating a sample of the maleic acid based copolymer from Example 1 at a suitable concentration, either in water or in isotonic saline at above pH 7.0, and mixing it by means of mechanical agitation with a hydrated sample of a selected phospholipid, either DPPC or DLPC, until a homogeneous suspension results. Using DPPC it will be necessary of course to maintain the mixture at an elevated temperature above the main phase transition temperature. e.g. at about 50° C., at this stage. The pH is then reduced until the pH is between 3 and 5, at which point the suspension will spontaneously clear indicating the formation of micellar structures of smaller dimensions than those of the wavelength of visible light.

The resultant clear and transparent colourless solution can be cooled if necessary, e.g. if DPPC is present, and can be adjusted to the desired pH by the addition of either sodium hydroxide (0.1M) or hydrochloric acid (0.1M). Once the desired pH is obtained the solution can be freeze-dried for storage.

A similar procedure is adopted with three component systems in which a fatty acid ester, or another polymer such as PLETESA, or a substance to be solubilized and/or transported in the lipid component of the micellar complexes, is also added to the mixture before lowering the pH.

Testing

For checking and testing the properties of compositions of polymer/phospholipid complexes in accordance with the invention, a number of examples were prepared and the results of various tests of surface activity characteristics carried out for some of these are shown in Tables hereinafter referred to. To facilitate carrying out experiments at room temperature rather than at an elevated temperature, most of the complexes prepared and tested were based on the use of dilaurylphosphatidylcholine (DLPC) as the membrane-forming phospholipid rather than dipalmitoylphosphalidylcholine (DPPC) since at room temperature DLPC is above its phase transition temperature in a liquid crystalline state. Thus, molecules of DLPC readily assemble into bilayers when mixed with the amphipathic polymers. As already noted, using DPPC it is generally necessary for reactions and testing to be carried out at a much higher temperature, above its phase transition temperature of about 42° C., although in the final product DPPC could be preferable because of better surface activity or stability characteristics.

Complexes that have been prepared and tested include a number of complexes formed from DPPC or DLPC and poly(maleic acid styrene) (PMAS), poly(maleic acid butyl vinyl ether) (PMBE), or poly(maleic acid propyl vinyl ether) (PMPE).

One of the most important properties of the polymer/ phospholipid complexes in accordance with the invention, especially for use as artificial lung surfactants, is the manner in which the surface tension varies with repetitive changes in surface area, and one test method that has been used is a pulsating bubble technique using a pulsating bubble surfactometer which consists of a sample chamber, pulsator unit and pressure-recording device. In a particular example, the sample chamber is made up of a capillary tube (ID 0.5 mm) inserted into a wider diameter tube (ID 1.5 mm). The latter is filled with the sample liquid and connected to a pulsator unit and pressure transducer. Air is drawn in through the capillary tube which acts as an airways forming a bubble of air within the sample chamber. This bubble serves as a model alveolus. The column of liquid within the sample chamber is raised and lowered by a small diameter piston connected to a synchronous motor which enables the surface area to be repeatedly reduced to 50% of its original volume. Variations of pressure within the bubble, during each pulsation cycle, are measured by a transducer and combined with values of bubble volume to calculate changes in surface tension.

This pulsating bubble technique simulates to some extent the contraction and expansion of the alveoli sacks in the lungs and allows the surface tension to be assessed at minimum and maximum bubble volumes, and allows the effect of repeated expansion and compression cycles upon the adsorption of surface active components to be observed and quantified. This technique has been used as a model in vitro system for testing the efficacy of synthetic lung surfactants. Some results of tests carried out not only on the complexes prepared in accordance with the invention, but also on the membrane-forming phospholipids used and the polymers themselves, as well as on commercially available lung surfactants, are summarised in the Tables at the end of the present description.

Pulsating bubble surfactometr control experiments were first conducted with the compositions listed in Table II on their own. None of the polymers used in these control experiments, when tested in aqueous solution, showed any significant surface activity. In contrast, the commercial surfactants that contain animal derived apoproteins, Curosurf™ and Survanta™, were found rapidly to develop excessively low surface tensions after relatively short periods of pulsing (5 minutes), as shown in Table I.

When PMAS was combined with the phospholipid DLPC in a two-component system, low surface tension values were recorded after 5 minutes pulsing at pH 4.9 (see Table III). Similar low surface tension values were also obtained with DLPC/PMBE complexes, with the lowest values after 5 minutes pulsing being recorded when using 2.5% DLPC tested at pH 4.17 with a lipid/polymer ratio of 10:1. A low surface tension was also observed with the DLPC/PMPE surfactant complexes when tested at 2.5% in a 1:1 ratio at pH 4.30, as is also shown in Table III although a somewhat longer pulsing period was required. Similar results are shown in Table TV obtained with three component surfactant complexes. Further results are shown in Table V.

These results in Tables III, IV and V indicate a high suitability for use as artificial lung surfactants. It may be stressed that these synthetic assemblies contrast with the commercial lung surfactants based on animal derived proteins for which long term, potentially allergic, responses are as yet undefined.

Applications Related to Drug Delivery

The synthetic surfactants described also have the ability to deliver conventional drugs, DNA or RNA or gene based pharmaceuticals locally to the lung, or via the highly permeable membranes lining the deep lung into the systemic circulation. The lipid-containing compositions containing the discoidal micellar assemblies described may therefore be used to deliver drugs for the treatment of pulmonary disease or for transport into the systemic circulation for use in treating systemic disease.

Alternatively, suitable formulations of the compositions described containing the micellar systems of sub-liposomal dimensions, could be directly injected into the systemic circulation for delivery or active targeting of drugs contained within the bilayer core. If these compositions are made using the relatively low molecular weight copolymer PMAS hereinbefore referred to, although this is non-degradable as pointed out it has been previously used in medicine and is likely to be readily excreted through the kidneys. As for the phospholipid DPPC, this is endogenous to the body, and in any event is likely to be broken down fairly readily in the body without causing serious problems.

Already using compositions in accordance with the invention, several aqueous insoluble drug entities have been successfully incorporated into micellar assemblies and solubilized. To enable site specific targeting, it is also possible additionally to incorporate biological ligands (e.g. antibodies, receptors) into the micellar assemblies. Other drugs having poor aqueous solubility that are possible candidates for incorporation, solubilization and delivery in phospholipid micellar assemblies of compositions of the present invention include taxol and quercetin. It can also be possible to incorporate a DNA plasmid into the core of the micellar assemblies for use in gene therapy and, in addition, it is quite feasible to incorporate CD4 receptors during preparation. Such CD4 receptors could protrude above the plane of the bilayer membrane of the micellar assemblies and allow active targeting to particular cellular regions.

EXAMPLE 3

An example of the use of complexes of phospholipicis and amphipathic associating polymers in compositions made in accordance with the invention for delivery of drugs with a potential to target particular body areas is provided by the successful solubilization of the anti-cancer agent CB 1954 into a DLPC/PMAS complex at the 1% level.

In this Example, a formulation to solubilize the aqueous insoluble cytotoxic drug CB 1954: 5-(azinidin-1-yl)-2,4-dinitrobenzamide into a DLPC/PMAS micelle is made as follows:

1 ml of 2% DLPC (20 mg) is hydrated in HPLC grade water and to this solution is added 1 mg of CB1954. The mixture is then mixed with 1 ml of a 2% solution of PMAS (20 mg) at pH 6.2 to give a final concentration by weight of 1% DLPC, 0.05% CB1954 and 1% PMAS in 2 mls which forms a turbid solution. The pH of this solution is lowered towards pH 3 and then raised to pH 5.8 after which the solution clears and is adjusted to pH 7.0.

EXAMPLE 4

An example of the formulation of compositions made in accordance with the invention for the targeted delivery of drugs into the lung or into the systemic circulation is provided by the following corticosteroid formulation:

| DLPC | 2.5% |
| --- | --- |
| PMAS | 0.25% |
| Dexamethasone | 0.25% |
| methyl hydroxy benzoate | 0.3% |
| propyl hydroxy benzoate | 0.3% |
| sodium chloride | 0.8% |
| purified water | q.s. |
| pH | 5.5 |

EXAMPLE 5

An example of the potential formulation of compositions made in accordance with the invention for the delivery of an antifungal drug, either in a medical or a non-medical application, is provided by the following antifungal formulation:

| DLPC | 2.5% |
| --- | --- |
| PMAS | 0.25% |
| amphotericin B | 0.25% |
| methyl hydroxy benzoate | 0.3% |
| propyl hydroxy benzoate | 0.3% |
| sodium chloride | 0.8% |
| purified water | q.s. |
| pH | 5.5 |

Other Applications

Apart from drug delivery, pharmaceutically acceptable formulations of the compositions in accordance with the invention can also be used to treat or lubricate surfaces of damaged or diseased articulated joints, e.g. by intra-articular injection, and may also be used to coat and treat surfaces of medical devices and prostheses, e.g. artificial joints or contact lenses.

By way of further example, set out below is a typical ophthalmic or ocular formulation to treat dry eye syndrome, to coat contact lenses, or for incorporation into contact lens care products.

EXAMPLE 6

| DLPC | 2.5% |
| --- | --- |
| PMAS | 0.25% |
| methyl hydroxy benzoate | 0.3% |
| propyl hydroxy benzoate | 0.3% |
| sodium chloride | 0.8% |
| purified water | q.s. |
| pH | 5.5 |

Other examples relating to the solubilising properties of the compositions in accordance with the invention are referred to below.

The solubilising ability of the polymer/lipid micellar system can be further enhanced by incorporation of additional surfactants. This can be especially useful when solubilising excessively hydrophobic materials where the solubilising ability of the PMAS is insufficient to form a stable aqueous solution. In this case the incorporation of surfactants such as toxicologically acceptable polyethylene oxide/polypropylene oxide block copolymers (available from BASF Corporation and sold under the trade names Pluronic and Tetronic), can result in marked improvement in the solubilisation obtained.

EXAMPLE 7

This represents one example of a formulation of the above kind and consists of:

(a) A mixture of lipids containing lecithin (diacyl phosphatidylcholine) as available from International Speciality Products ISP (USA) and sold under the trade mark ProLipid 141 (this mixture also includes Behenyl alcohol, $C_{12}$–$C_{16}$ alcohols, stearic and palmitic acids and glyceryl stearate in addition to lecithin), used at 0.1% wt/wt;

(b) PMAS from Aldrich Chemical Co. (USA), Cat. No. 43,529-5, used at 0.5% wt/wt;

(c) Pluronic grade L64 (BASF Corp.), used at 0.25% wt/wt.

This formulation shows limited solubilising ability above pH 7 but as the pH is lowered to below a critical pH of 3–4 at which conformational changes occur within the PMAS then solubilisation of the hydrophobic material occurs. The presence of the Pluronic copolymer also prevents precipitation of the PMAS as the pH is lowered below pH 3 indicating some emulsification of the PMAS.

It may be noted that compositions of this invention containing membrane-forming polar lipid, surfactant and a synthetic amphipathic polymer such as poly(maleic acid-styrene) (PMAS) may also be advantageously incorporated into monomer mixes used in making hydrogels, prior to their polymerisation, thereby to form a semi-interpenetrating polymer network or SIPN. Such PMAS-containing hydrophobes exhibit a change in their surface characteristics upon contact with micellar hydrophobes since the amphipathic polymer at the surface appears to reorientate to expose hydrophobic portions of the molecule. This effect may enable surface components to be selectively adsorbed e.g. simple surfactants, polymeric surfactants and hydrophobe/surfactant mixtures. In the latter case it may be noted that surface components partially replace the phospholipid as the film forming agent.

As previously indicated, compositions in accordance with the invention may also have many other useful applications, especially in connection with the solubilization of lipid soluble substances that have poor aqueous solubility, and the invention may be particularly applicable in this respect in the cosmetics industry, and also in the food industry where problems are frequently encountered in dissolving lecithin phospholipids or other amphipathic lipids and water insoluble substances, e.g. in the manufacture of lotions, creams, sauces and like materials of colloidal form.

The polymer/lipid micellar assemblies described herein can also be used as a platform for incorporation of membrane, receptor or lipodial proteins in order to maintain the proteins within a physiologically valid phospholipid bilayer environment where they retain their native conformation while at the same time solubilising them in an aqueous environment. In this environment the structure of such proteins can be determined by spectroscopic methods such as proton NMR spectroscopy. This offers a marked advantage over existing solid phase techniques which are considerably less sensitive and thereby will enable improved structural resolution and more effective design of potential drug molecules or assessment of drug binding.

It will be seen that the invention presents a number of different aspects and it should be understood that it embraces within its scope all novel and inventive features and aspects herein disclosed, either explicitly or implicitly and either singly or in combination with one another. Also, many detail modifications are possible and, in particular, the scope of the invention is not to be construed as being limited by the illustrative example(s) or by the terms and expressions used herein merely in a descriptive or explanatory sense.

Pulsating Bubble Surfactometry—Results

Showing minimum Surface Tension (ST) value achieved and time to reach this level.
Pulse Rate (PR)=34, Temp=Room Temp & pH=7.0 unless otherwise stated.
Key to Abbreviations DLPC = Dilaurylphosphatidylcholine
PMAS = Poly(maleic acid styrene)
PMBE = Poly(maleic acid butyl vinyl ether)
PMPE = Poly(maleic acid propyl vinyl ether)
PMEE = Poly(maleic acid ethyl vinyl ether)
PAAEA = Poly(acrylic acid ethyl acrylate)
LALE = Lauric acid lauryl ester
PLETESA-P = Poly(lysine ethyl ester adipamide) - palmitamide

TABLE I

Surface Properties of Commercially Available Artificial Lung Surfactants
The following data shows the minimum surface tension (ST) value achieved and time taken to reach this level. Solutions with an ability to lower the surface tension to less than 5 dynes/cm in 20 minutes or less of pulsing are considered to be effective surfactants.

| Composition (wt./wt.) | % | Minimal ST dynes/cm | Time to Develop (mins) |
|---|---|---|---|
| Curosurf+ | 1.35% | 3.73 | 5 |
| Survanta* | 2.50% | 1.05 | 5 |
| Survanta | 2.50% | 0.42 | 5 |
| Survanta | 2.50% | 0.00 | 5 |
| Survanta | 1.35% | 4.16 | 5 |

+Trade Mark - Serono Inc.
*Trade Mark - Abbott Laboratories

TABLE II

Controls

| Composition (wt./wt.) | % | pH | Minimal ST dynes/cm | Time to Develop (mins) | Comments |
|---|---|---|---|---|---|
| DLPC | 2.5 | | 9.60 | 30 | Sonicated |
| DLPC | 1.0 | 3.22 | 6.39 | 30 | PR = 12 |
| DLPC | 1.0 | 9.33 | 15.66 | 30 | PR = 12 |
| DLPC | 1.0 | | 6.82 | 20 | 2 hrs hydration |
| DLPC | 1.0 | | 24.89 | 30 | 12 hr hydration |
| DPLC | 1.0 | 12.00 | 15.10 | 30 | |
| PMAS | 0.67 | 6.74 | 16.93 | 25 | |
| PMAS | 0.50 | 5.05 | 28.39 | 5 | |
| PMAS | 0.50 | 7.96 | 32.90 | 5 | |
| PMAS | 0.50 | 9.90 | 40.10 | 5 | |
| PMAS | 2.50 | 7.3 | 19.41 | 30 | |
| PMBE | 1.0 | | 27.35 | 10 | PR = 12 |
| | 2.5 | | 40.88 | 10 | |
| | 1.0 | 4.3 | 24.07 | 5 | |
| | 1.0 | 7.0 | 9.90 | 15 | |
| PMPE | 2.5 | | 22.85 | 15 | |
| PMEE | 2.5 | | 30.33 | 15 | |
| PAAEA | 0.25 | 4.5 | 30.38 | 5 | |
| | 0.25 | 6.0 | 28.37 | 5 | |
| | 0.25 | 7.1 | 27.84 | 5 | |
| | 0.25 | 8.48 | 23.64 | 5 | |
| LALE | 1.0 | | 22.61 | 30 | |
| PLETESA-P | 1.0 | | 25.10 | 30 | |

TABLE III

Phospholipid/Polymer Complexes DLPC - PMAS/PMBE/PMPE in Two Component Systems

| Composition % (wt./wt.) | pH | Minimal ST dynes/cm | Time to Develop (mins) | Comments |
|---|---|---|---|---|
| DLPC/PMAS | | | | |
| 0.5/1.25 | 4.9 | 3.32 | 5 | |
| DLPC/PMBE | | | | |
| 1.0/2.5 | 6.90 | 0.00 | 20 | |
| DLPC/PMBE | | | | |
| 1.0/0.5 | 7.78 | 0.43 | 20 | PR = 12 |
| 1.0/0.5 | 6.10 | 3.32 | 20 | PR = 12 |
| DLPC/PMBE | | | | |
| 2.5/0.25 | 4.17 | 4.48 | 5 | |
| 2.5/0.25 | | 1.57 | 10 | |

TABLE III-continued

Phospholipid/Polymer Complexes DLPC - PMAS/PMBE/PMPE in Two Component Systems

| Composition % (wt./wt.) | pH | Minimal ST dynes/cm | Time to Develop (mins) | Comments |
|---|---|---|---|---|
| DLPC/PMBE | | | | |
| 1.0/0.1 | 4.82 | 3.25 | 20 | PR = 12 |
| DLPC/PMPE | | | | |
| 2.5/2.5 | 4.30 | 0.00 | 20 | |
| 2.5/2.5 | 7.00 | 3.86 | 15 | |

TABLE IV

Phospholipid/Polymer Complexes DLPC - PMAS/LALE/PLETESA - PALMITAMIDE (PP) in Three Component Systems

| Composition (wt./wt.) | % | pH | Minimal ST dynes/cm | Time to Develop (Mins) | Comments |
|---|---|---|---|---|---|
| DLPC/PMAS/LALE | 0.31/0.31/0.02 | | 0.20 | 1 | |
| DLPC/PMAS/PP | 0.5/0.5/0.05 | 6.13 | 1.67 | 20 | |
| DLPC/PMAS/PP | 1.0/1.0/0.5 | 5.62 | 3.15 | 20 | PR = 12 |
| DLPC/PMAS/PP | 1.0/1.0/0.5 | 6.31 | 1.04 | 20 | |

TABLE V

| Code | Lipid/Polymer | Composition | pH | Temp °C. | Minimal ST <10 dynes/cm | Time to Develop | Comment |
|---|---|---|---|---|---|---|---|
| Control Phospholipids and DLPC - Dilauryl Phosphatidylcholine Recombinants | | | | | | | |
| dlfs7 | DLPC (fresh) | 0.5 | 7.12 | 25.1 | 18.25 | 20 | |
| dlf5 | DLPC (fresh) | 0.5 | 5.47 | 24.0 | 12.57 | 20 | |
| | DLPC (fresh) | 0.5 | 5.47 | 24.0 | 0.04 | 40 | |
| dlfs5 | DLPC (fresh) sonicated | 0.5 | 5.47 | 24.8 | 1.61 | 7 | |
| dlfs4 | DLPC (fresh) sonicated | 0.5 | 3.92 | 24.0 | 1.67 | 10 | |
| dlpf7 | DPPC sonicated | 0.5 | 7.3 | 23.1 | 20.36 | 40 | |
| dlpf6 | DPPC (fresh) | 0.5 | 6.3 | 24.9 | 16.18 | 30 | |
| dlpf4 | DPPC | 0.5 | 4.1 | 21.9 | 5.31 | 30 | |
| dpf7s | DPPC sonicated | 0.5 | 7.3 | 24.0 | 9.99 | 20 | |
| | DPPC sonicated | 0.5 | 7.3 | 37.5 | 27.95 | 40 | after 40 mins at room temp |
| dp7st | DPPC sonicated | 0.5 | 7.3 | 37.5 | 26.58 | 2 | |
| dlst3 | DLPC/PMA-IH | 0.5/0.2 | 5.34 | 23.3 | 17.61 | 40 | |
| dlst2 | DLPC/PMA-IH | 0.5/0.1 | 5.7 | 23.1 | 2.33 | 10 | |
| dlst1 | DLPC/PMA-IH | 0.5/0.05 | 5.6 | 21.9 | 8.93 | 30 | |
| dlst4 | DLPC/PMA-IH | 0.2/0.4 | 5.8 | 23.5 | 14.66 | 40 | |
| dlst6 | DLPC/PMA-IH | 0.1/0.5 | 5.5 | 23.9 | 7.93 | 40 | |
| dlst5 | DLPC/PMA-IH | 0.1/0.5 | 7.5 | 22.9 | 6.12 | 30 | |
| dlih1 | DLPC/PMA-IH | 0.5/0.5 | 7.53 | 22.7 | 19.47 | 10 | (12/min pulse r) |
| | | | | | 11.04 | 10 | (30/min pulse r) |
| | | | | | 1.67 | 45 | (30/min pulse r) |
| 5dlst | DLPC/PMA-IH | 0.5/0.5 | 7.34 | 24.4 | 12.52 | 40 | |
| dlih7 | DLPC/PMA-IH | 0.5/0.5 | 7.3 | 23.5 | 16.04 | 30 | |
| 7dlst | DLPC/PMA-IH | 0.5/0.5 | 7.2 | 21.6 | 14.89 | 30 | |
| dli5/dlpi1 | DLPC/PMA-IH | 0.5/0.5 | 5.6 | 23.6 | 6.12 | 40 | |
| 52dst | DLPC/PMA-IH | 0.5/0.5 | 5.6 | 22.0 | 7.69 | 20 | stored |
| 53dst | DLPC/PMA-IH | 0.5/0.5 | 5.6 | 22.5 | 7.44 | 10 | |
| | | | | 37.2 | 5.07 | 2 | |
| 54dst | DLPC/PMA-IH | 0.5/0.5 | 5.6 | 37.2 | 3.08 | 5 | |
| dl5/dlin5 | DLPC/PMA-IH | 0.5/0.5 | 5.5 | 24.3 | 8.15 | 5 | |
| dlin4 | DLPC/PMA-IH | 0.5/0.5 | 4.3 | 23.3 | 9.21 | 2 | |
| dlal7 | DLPC/PMA-ald | 0.5/0.5 | 7.2 | 26.0 | 7.06 | 20 | |
| dla7_r | DLPC/PMA-ald | 0.5/0.5 | 6.9 | 23.9 | 17.76 | 40 | (overnight 20 C.) |
| dlal5 | DLPC/PMA-ald | 0.5/0.5 | 5.37 | 25.2 | 7.79 | 30 | |
| dlal5_r/dla5_r | DLPC/PMA-ald | 0.5/0.5 | 5.3 | 22.7 | 5.82 | 20 | (overnight 20 C.) |
| dlal4 | DLPC/PMA-ald | 0.5/0.5 | 4.3 | 26.2 | 2.73 | 2 | |
| Lipids Other Than DLPC - Dilauryl Phosphatidylcholine | | | | | | | |
| dpih1 | DPPC/PMA-IH | 0.5/0.5 | 7.2 | 22.7 | 52.78 | 30 | |
| dpih5 | DPPC/PMA-IH | 0.5/0.5 | 4.87 | 23.4 | 44.17 | 10 | |
| dpih4 | DPPC/PMA-IH | 0.5/0.5 | 3.89 | 23.4 | 33.91 | 25 | |
| dpih73 | DPPC/PMA-IH | 0.5/0.5 | 7.2 | 35.0 | 31.85 | 30 | |
| dpih53 | DPPC/PMA-IH | 0.5/0.5 | 5.3 | 35.0 | 45.15 | 30 | |
| 56dst | DPPC/PMA-IH | 0.5/0.5 | 7.43 | 37.4 | 56.19 | 2 | fresh DPPC |
| 55dst | DPPC/PMA-IH | 0.5/0.5 | 5.36 | 37.4 | 47.46 | 40 | fresh DPPC |
| 57dst | DPPC/PMA-IH | 0.5/0.5 | 4.53 | 37.3 | 41.39 | 2 | fresh DPPC overheat 88° C. |
| dpst7 | DPPC/PMA-ald | 0.5/0.5 | 7.3 | 23.1 | 50.69 | 40 | |

TABLE V-continued

| Code | Lipid/ Polymer | Composition | pH | Temp °C. | Minimal ST <10 dynes/ cm | Time to Compdevelop ment |
|---|---|---|---|---|---|---|
| dps53 | DPPC/ PMA-ald | 0.5/0.5 | 5.4 | 37.5 | 18.34 | 10 |
| dpst5 | DPPC/ PMA-ald | 0.5/0.5 | 5.3 | 22.9 | 6.52 | 40 |
| dpst4 | DPPC/ PMA-ald | 0.5/0.5 | 4.1 | 23.0 | 35.26 | 30 |
| list5 | Lino.A./ PMA-IH | 0.5/0.5 | 5.5 | 25.3 | 31.24 | 30 |
| list7 | Lino.A./ PMA-IH | 0.5/0.5 | 7.3 | 25.3 | 26.01 | 30 |
| stst7 | Stearic/ PMA-IH | 0.5/0.5 | 7.2 | 24.7 | 23.12 | 30 |
| stst5 | Stearic/ PMA-IH | 0.5/0.5 | 5.3 | 25.1 | 28.59 | 30 |
| pma-sd | SDS/ PMA-ald | 0.1/0.5 | | 24.8 | 27.38 | 40 |

KEY:
DLPC—Dilauryl phosphatidylcholine
DPPC—Dipalmitoyl phosphatidylcholine
Lino.A.—Linoleic acid
PMA-IH—Poly(maleic acid/styrene) synthesised in-house
PMA-ald—Poly(maleic acid/styrene) ex. Aldrich Chem. Co.
SDS—Sodium dodecyl sulphate
ST—Surface Tension mN/m
Stearic—Stearic acid
Pulse Rate = 30/min unless otherwise stated.

What is claimed is:

1. A lipid-containing composition having a visual appearance of a substantially clear solution comprising,
a membrane-forming polar lipid dispersed in an aqueous medium together with a synthetic amphipathic polymer that interacts with the polar lipid to produce a polymer/lipid complex,
whereby said polymer interacts with and solubilizes the polar lipid in the aqueous medium at a pH which is below a critical lipid-solubilizing value and at a temperature above a predetermined phase transition temperature dependant upon the polar lipid,
such that said polymer/lipid complex is in the form of non-liposomal micellar particles or assemblies of discoidal form in which the polar lipid forms a bilayer core;
said composition being pH variable, such that the pH can be raised from below the critical lipid-solubilizing value to above the critical lipid-solubilizing value by addition of alkaline reagent;
said synthetic amphipathic polymer being a non-block copolymer having a linear backbone along which hydrophobic groups and anionic hydrophilic groups are evenly arranged, and comprising a first monomer which is an unsaturated dicarboxylic acid or anhydride thereof, and a second monomer which is a monoeneoic compound, said first and second monomers being arranged in alternating relationship along the linear backbone, with the proviso that, if the second monomer is an alkyl vinyl ether, the alkyl group thereof has from 2 to 8 carbon atoms, and, wherein the number of carbon atoms in the hydrophobic side groups of the amphipathic polymer is equal to or greater than the number of carbon atoms in the polymer backbone.

2. The lipid-containing composition according to claim 1, wherein said lipid soluble target compound comprises a drug or a bioactive therapeutic agent.

3. A lipid-containing composition having a visual appearance of a substantially clear solution comprising,
a membrane-forming polar lipid dispersed in an aqueous medium together with a lipid-soluble target substance of poor aqueous solubility and a synthetic amphipathic polymer that interacts with the polar lipid to produce a polymer/lipid complex and solubilize the target substance and the polar lipid in the aqueous medium while the pH is below a critical lipid-solubilizing value and while the temperature is above a predetermined phase transition temperature dependant upon the polar lipid,
such that said polymer/lipid complex is in the form of non-liposomal micellar particles or assemblies of discoidal form in which the polar lipid forms a bilayer core;
said composition being pH variable, such that the pH can be raised from below the critical lipid-solubilizing value to above the critical lipid-solubilizing value by addition of alkaline reagent;
said synthetic amphiphilic polymer having a linear backbone along which hydrophobic groups and anionic hydrophilic groups are evenly arranged, and comprising
(i) a polycarboxylic acid homopolymer in which the hydrophobic groups are pendant side groups, or
(ii) a copolymer, other than a block copolymer, comprising a first monomer which is an unsaturated dicarboxylic acid or anhydride thereof, and a second monomer which is a monoenoic compound, said first and second monomers being arranged in alternating relationship along the linear backbone, with the proviso that, if the second monomer is an alkyl vinyl ether, the alkyl group thereof has from 2 to 8 carbon atoms and,
wherein the number of carbon atoms in the hydrophobic side groups of the amphipathic polymer is equal to or greater than the number of carbon atoms in the polymer backbone.

4. The lipid-containing composition according to claim 3, wherein said synthetic amphipathic polymer is a homopolymer of 2-ethylacrylic acid or 2-propylacrylic acid.

5. The lipid-containing composition according to claim 1 or 3, wherein said synthetic amphipathic polymer is said copolymer wherein said second monomer is a compound of formula R—CH=CH$_2$, wherein R is hydrogen, alkyl with 1 to 8 carbon atoms, alkoxy with 2 to 8 carbon atoms, phenyl, benzyl, phenyl, or benzyl substituted with alkyl or another hydrophobic group.

6. The lipid-containing composition according to claim 5, wherein R is alkoxy with from 3 to 6 carbon atoms.

7. The lipid-containing composition according to claim 5, wherein said first monomer is a compound of formula:

wherein $R^1$ and $R^2$ are each, independently, hydrogen or $C_1$–$C_9$ alkyl, at least one of $R^3$ and $R^4$ is hydrogen and the other is hydrogen or $C_2$–$C_9$ alkyl, and the copolymer structure is such that the second monomer units alternate with the dicarboxylic acid or half-ester units providing a regular arrangement of alternate pendant anionic hydrophilic side groups and hydrophobic side groups along the linear backbone, subject to the proviso that if, in the second monomer, R is hydrogen or is ethoxy, $R^3$ and $R^4$ are not both hydrogen.

8. The lipid-containing composition according to claim 7, wherein $R^1$ and $R^2$ are both hydrogen and R, if alkyl, contains less than 8 carbon atoms.

9. The lipid-containing composition according to claim 1 or claim 3, wherein the average charge ratio per backbone carbon of the amphipathic polymer, when ionized, is less than or equal to unity.

10. The lipid-containing composition according to claim 1 or claim 3, wherein said synthetic amphipathic polymer is an alternating copolymer of maleic acid or anhydride thereof with styrene, indene, a $C_{1-4}$ alkyl substituted styrene or indene, or with an alkyl vinyl ether selected from the group consisting of propyl vinyl ether, isopropyl vinyl ether and butyl vinyl ether.

11. The lipid-containing composition according to claim 1 or claim 3, wherein the synthetic amphipathic polymer has a balance of hydrophobic and anionic hydrophilic groups evenly arranged along a linear backbone.

12. The lipid-containing composition according to claim 1 or claim 3, wherein said lipid comprises a phospholipid.

13. The lipid-containing composition according to claim 12, wherein the phospholipid is a glycerol ester of phosphatidic acid having non-polar acyl ester groups containing 8 to 25 carbon atoms.

14. The lipid-containing composition according to claim 12, wherein the phospholipid is a phosphatidylcholine.

15. The lipid-containing composition according to claim 12, wherein the phospholipid is dipalmitoylphosphatidylcholine, dilauroylphosphatidylcholine or dimyristoylphosphatidylcholine.

16. The lipid-containing composition according to claim 1 or claim 3, wherein the synthetic amphipathic polymer is physiologically non-toxic and pharmacologically acceptable and may be safely administered to mammals.

17. The lipid-containing composition according to claim 1 or claim 3, wherein the synthetic amphipathic polymer has a number average molecular weight in the range of from 2,000 to 500,000 daltons.

18. The lipid-containing composition according to claim 1 or claim 3, wherein the synthetic amphipathic polymer has a number average molecular weight in the range of from 2,000 to 50,000 daltons.

19. The lipid-containing composition according to claim 1 or claim 3, wherein the synthetic amphipathic polymer is a poly(maleic acid-styrene) copolymer.

20. The lipid-containing composition according to claim 1 or claim 3, wherein the solubilizing micellar particles or assemblies formed by the polymer/lipid complex in the aqueous medium have a maximum diameter or cross-sectional dimension of less than 50 nanometers under physiological conditions of temperature and pH.

21. The lipid-containing composition according to claim 1 or claim 3, further comprising at least one additional surfactant to enhance the solubilizing property thereof.

22. A formulation suitable for pharmaceutical use comprising the lipid-containing composition according to claim 1 or claim 3 admixed with one or more of pharmaceutically acceptable carriers, additives, diluents or excipients.

23. The formulation according to claim 22, which is a sterile aqueous preparation and is suitable for parenteral administration.

24. A hydrogel containing a semi-interpenetrating polymer network produced by polymerizing a hydrogel composition containing the lipid-containing composition as claimed in claim 1 or 3.

25. A method of preparing a lipid-containing composition as claimed in claim 1 or claim 3, which comprises mixing the synthetic amphipathic polymer and the polar lipid in an aqueous medium at a pH above said critical solubilizing value thereby forming a cloudy or turbid aqueous dispersion, and then treating the mixture with an acidifying agent to lower the pH below said critical solubilizing value while the temperature is above said predetermined phase transition temperature characteristic of the lipid, so that the synthetic amphipathic polymer solubilizes the polar lipid and causes the dispersion to clarify.

26. A lung surfactant formulation for use in the treatment of respiratory distress syndrome a lipid-containing composition comprising, a membrane-forming polar lipid dispersed in an aqueous medium together with a synthetic amphipathic polymer that interacts with the polar lipid to produce a polymer/lipid complex whereby the polymer interacts with and solubilizes the polar lipid in the aqueous medium while the pH is below a critical lipid-solubilizing value and while the temperature is above a predetermined phase transition temperature dependant upon the polar lipid, such that said polymer/lipid complex is in the form of non-liposomal micellar particles or assemblies of discoidal form in which the polar lipid forms a bilayer core;

said composition having a visual appearance of a substantially clear solution and being pH variable, such that the pH can be raised from below the critical lipid-solubilizing value to above the critical lipid-solubilizing value by addition of alkaline reagent;

said synthetic amphiphilic polymer having a linear backbone along which hydrophobic groups and anionic hydrophilic groups are evenly arranged, and comprising
  (i) a polycarboxylic acid homopolymer in which the hydrophobic groups are pendant side groups, or
  (ii) a copolymer, other than a block copolymer, comprising a first monomer which is an unsaturated dicarboxylic acid or anhydride thereof, and a second monomer which is a monoenoic compound, said first and second monomers being arranged in alternating relationship along the linear backbone, with the proviso that, if the second monomer is an alkyl vinyl ether, the alkyl group thereof has from 2 to 8 carbon atoms and, wherein the number of carbon atoms in the hydrophobic side groups of the amphipathic polymer is equal to or greater than the number of carbon atoms in the polymer backbone.

27. An ocular pharmaceutical formulation comprising a membrane-forming polar lipid dispersed in an aqueous medium together with a synthetic amphipathic polymer that interacts with the polar lipid to produce a polymer/lipid complex whereby the polymer interacts with and solubilizes the polar lipid in the aqueous medium while the pH is below a critical lipid-solubilizing value and while the temperature is above a predetermined phase transition temperature dependant upon the polar lipid, such that said polymer/lipid complex is in the form of non-liposomal micellar particles or assemblies of discoidal form in which the polar lipid forms a bilayer core;

said composition having a visual appearance of a substantially clear solution and being pH variable, such that the pH can be raised from below the critical lipid-solubilizing value to above the critical lipid-solubilizing value by addition of alkaline reagent;

said synthetic amphiphilic polymer having a linear backbone along which hydrophobic groups and anionic hydrophilic groups are evenly arranged, and comprising
  (i) a polycarboxylic acid homopolymer in which the hydrophobic groups are pendant side groups, or
  (ii) a copolymer, other than a block copolymer, comprising a first monomer which is an unsaturated dicarboxylic acid or anhydride thereof, and a second monomer which is a monoenoic compound, said first and second monomers being arranged in alternating relationship along the linear backbone, with the proviso that, if the second monomer is an alkyl vinyl ether, the alkyl group thereof has from 2 to 8 carbon atoms and,
wherein the number of carbon atoms in the hydrophobic side groups of the amphipathic polymer is equal to or greater than the number of carbon atoms in the polymer backbone.

28. A method of preparing a lipid-containing composition, which comprises:
  mixing a synthetic amphipathic polymer and a membrane-forming polar lipid in an aqueous medium at a pH above a critical solubilizing value thereby forming a cloudy or turbid aqueous dispersion, and
  treating the resulting mixture with an acidifying agent to lower the pH below said critical solubilizing value while the temperature is above a predetermined phase transition temperature characteristic of the lipid,
  whereby the synthetic amphipathic polymer interacts with and solubilizes the polar lipid to produce a polymer/lipid complex in the form of non-liposomal micellar particles or assemblies of discoidal form in which the polar lipid forms a bilayer core and clarifies the dispersion, said composition thereby having a visual appearance of a substantially clear solution;
  said synthetic amphiphilic polymer having a linear backbone along which hydrophobic groups and anionic hydrophilic groups are evenly arranged, and comprising
    (i) a polycarboxylic acid homopolymer in which the hydrophobic groups are pendant side groups, or
    (ii) a copolymer, other than a block copolymer, comprising a first monomer which is an unsaturated dicarboxylic acid or anhydride thereof, and a second monomer which is a monoenoic compound, said first and second monomers being arranged in alternating relationship along the linear backbone, with the proviso that, if the second monomer is an alkyl vinyl ether, the alkyl group thereof has from 2 to 8 carbon atoms and,
  further comprising,
    after the dispersion clears, reducing the temperature below said phase transition temperature to stablize the solution, and
    treating the clear solution with an alkaline reagent to raise the pH to a final value above said critical lipid solubilizing value.

29. A method of solubilizing a lipid-soluble target compound having poor aqueous solubility, in an aqueous medium, said method comprising,
  mixing, in said aqueous medium, the target substance, a membrane-forming polar lipid and a synthetic amphipathic polymer, at a pH above a critical solubilizing value, thereby forming a cloudy or turbid aqueous dispersion, and
  treating the resulting mixture with an acidifying agent to lower the pH below said critical solubilizing value while the temperature is above a predetermined phase transition temperature characteristic of the lipid,
  whereby the synthetic amphipathic polymer interacts with and solubilizes the polar lipid together with the target substance, in the aqueous medium, to produce a polymer/lipid complex in the form of non-liposomal micellar particles or assemblies of discoidal form in which the polar lipid forms a bilayer core and clarifies the dispersion;
  said synthetic amphiphilic polymer having a linear backbone along which hydrophobic groups and anionic hydrophilic groups are evenly arranged, and comprising
    (i) a polycarboxylic acid homopolymer in which the hydrophobic groups are pendant side groups, or
    (ii) a copolymer, other than a block copolymer, comprising a first monomer which is an unsaturated dicarboxylic acid or anhydride thereof, and a second monomer which is a monoenoic compound, said first and second monomers being arranged in alternating relationship along the linear backbone, with the proviso that, if the second monomer is an alkyl vinyl ether, the alkyl group thereof has from 2 to 8 carbon atoms.

30. A method for therapeutically treating a mammal in need thereof, which comprises, administering to said mammal a therapeutically effective amount of a lipid-containing liquid composition in which a membrane-forming polar lipid is dispersed together with a synthetic amphipathic polymer that interacts with the polar-lipid to produce a polymer/lipid complex which is soluble in the aqueous medium at a pH which is below a critical lipid-solubilizing value and at a temperature which is above a predetermined phase transition temperature, which is dependant upon the polar lipid,
  said composition being pH variable, such that the pH can be raised from below the critical lipid-solubilizing value to above the critical lipid-solubilizing value by addition of alkaline reagent;
  said composition having the visual appearance of a substantially clear solution;
  said polymer/lipid complex being in the form of non-liposomal micellar particles or assemblies of discoidal form in which the polar lipid forms a bilayer core;
  said synthetic amphiphilic polymer having a linear backbone along which hydrophobic groups and anionic hydrophilic groups are evenly arranged, and comprising
    (i) a polycarboxylic acid homopolymer in which the hydrophobic groups are pendant side groups, or
    (ii) a copolymer, other than a block copolymer, comprising a first monomer which is an unsaturated dicarboxylic acid or anhydride thereof, and a second monomer which is a monoenoic compound, said first and second monomers being arranged in alternating relationship along the linear backbone, with the proviso that, if the second monomer is an alkyl vinyl ether, the alkyl group thereof has from 2 to 8 carbon atoms and,
  wherein the number of carbon atoms in the hydrophobic side groups of the amphipathic polymer is equal to or greater than the number of carbon atoms in the polymer backbone.

31. A method according to claim 30, wherein said lipid-containing liquid composition further comprises a lipid-soluble target substance which has poor aqueous solubility and which is a drug or a bioactive therapeutic agent and, wherein said target substance is solubilized in the presence of said polymer/lipid complex.

32. A lipid-containing liquid composition in which a membrane-forming polar lipid is dispersed in an aqueous medium together with copolymer of maleic acid or anhydride thereof, and styrene, to form a polymer/lipid complex in which said copolymer interacts with and solublizes the polar lipid in the aqueous medium while the pH is below a critical lipid solubilizing value and while the temperature is above a predetermined phase transition temperature dependeant upon the polar lipid, said composition being pH variable such that the pH can be raised from below said critical lipid-solubilizing value to above said critical lipid-solubilizing value by addition of alkaline reagent, said composition having a visual appearance of a substantially clear solution, and said polymer/lipid complex being in the form of non-liposomal micellar particles or assemblies of discoidal form in which the polar lipid forms a bilayer core.

* * * * *